United States Patent
Chen et al.

(10) Patent No.: US 9,251,581 B1
(45) Date of Patent: Feb. 2, 2016

(54) METHODS FOR PROMOTING SEMICONDUCTOR MANUFACTURING YIELD AND CLASSIFYING DEFECTS DURING FABRICATING A SEMICONDUCTOR DEVICE, AND COMPUTER READABLE MEDIUMS ENCODED WITH A COMPUTER PROGRAM IMPLEMENTING THE SAME

(75) Inventors: Shih-Tsung Chen, Taoyuan County (TW); Wei Fang, Milipitas, CA (US); Yu-Tsorng Fu, Taipei County (TW); Futang Peng, San Jose, CA (US); Zhao-Li Zhang, San Jose, CA (US)

(73) Assignee: HERMES MICROVISION, INC., Hsinchu (TW)

( * ) Notice: Subject to any disclaimer, the term of this patent is extended or adjusted under 35 U.S.C. 154(b) by 203 days.

(21) Appl. No.: 13/073,405

(22) Filed: Mar. 28, 2011

Related U.S. Application Data

(63) Continuation of application No. 12/881,425, filed on Sep. 14, 2010, now abandoned.

(51) Int. Cl.
*G06T 7/00* (2006.01)
*G01N 21/95* (2006.01)

(52) U.S. Cl.
CPC ............ *G06T 7/001* (2013.01); *G01N 21/9501* (2013.01)

(58) Field of Classification Search
None
See application file for complete search history.

(56) References Cited

U.S. PATENT DOCUMENTS

| | | | |
|---|---|---|---|
| 7,570,796 B2 * | 8/2009 | Zafar et al. | 382/144 |
| 2004/0181769 A1 * | 9/2004 | Kochpatcharin et al. | 716/19 |
| 2005/0198602 A1 * | 9/2005 | Brankner | 716/8 |
| 2007/0156379 A1 * | 7/2007 | Kulkarni et al. | 703/14 |
| 2007/0280527 A1 * | 12/2007 | Almogy et al. | 382/149 |
| 2009/0136121 A1 * | 5/2009 | Nakagaki et al. | 382/149 |
| 2010/0208979 A1 * | 8/2010 | Abbott et al. | 382/149 |
| 2011/0307844 A1 * | 12/2011 | Abd Elkader et al. | 716/52 |

OTHER PUBLICATIONS

Yoda et al. "An Automatic Wafer Inspection System Using Pipelined Image Processing Techniques." IEEE Transactions on Pattern Analysis and Machine Intelligence, vol. 10, No. 1, Jan. 1988, pp. 4-16.*
Wikipedia article on GDSII, http://en.wikipedia.org/wiki/GDSII, accessed Oct. 29, 2013, 2 pages.*

* cited by examiner

*Primary Examiner* — Jon Chang
(74) *Attorney, Agent, or Firm* — Huffman Law Group, PC

(57) ABSTRACT

A method for promoting semiconductor manufacturing yield comprising the following steps and a computer readable medium encoded with a computer program implementing the method is provided. First, a processed layer is inspected to generate an inspected image with defects thereon. Next, the inspected image is aligned to an original design layout information of the processed layer. In addition, the defects are classified according to geometric features of the original design layout information of the processed layer and at least previous one layer and/or at least next one layer.

14 Claims, 5 Drawing Sheets

METHODS FOR PROMOTING SEMICONDUCTOR MANUFACTURING YIELD AND CLASSIFYING DEFECTS DURING FABRICATING A SEMICONDUCTOR DEVICE, AND COMPUTER READABLE MEDIUMS ENCODED WITH A COMPUTER PROGRAM IMPLEMENTING THE SAME

FIELD OF THE INVENTION

The present invention generally relates to semiconductor manufacturing, and more particularly to a method for classifying defects to promote semiconductor manufacturing yield.

DESCRIPTION OF THE RELATED ART

How to inspect defects in a semiconductor device is one of the major subjects in a semiconductor fabricating process. A conventional method for inspecting defects is using a scanning electron microscope (SEM) system to scan the semiconductor device layer by layer during a fabrication process of the semiconductor device, so as to capture scanned images, such as SEM images, of all layers, and then the presence of defects at each layer may be determined by inspecting the scanned images.

For example, the SEM system may be used to scan a patterned semiconductor layer after the patterned semiconductor layer is formed on a substrate, and thus the presence of defects at the patterned semiconductor layer may be determined by inspecting the scanned image of the patterned semiconductor layer. After that, the SEM system may also be used to scan a patterned metal layer after the patterned metal layer is formed on the patterned semiconductor layer. Thus, the presence of defects is determined layer by layer, and effect of each defect to the current inspected layer. i.e. the layer where the defect is located on, is determined. Accordingly, each defect may be classified into defect of interest (DOI) or unimportant defect, and thereby hot spots at each layer may be defined.

However, the above-mentioned inspecting method can only define effect of each defect to the current inspected layer, but effect of each defect to other layers or even to the whole device cannot be taken into consideration. In addition, each defect may be classified according to its effect to the current layer only, not the whole device, so that the classification and the hot spots defined according to the classification are limited. For example, a hot spot may result from specific patterns of the previous or the next layer affecting on some patterns of the current layer. Thus, only inspecting on patterns of the current layer may misjudge hot spot area, and lower classification precision.

Accordingly, it is highly desirable to provide a method for defining effects of defect to other layers and whole device.

SUMMARY OF THE INVENTION

The present invention is directed to a method for promoting semiconductor manufacturing yield according to geometric features of original design layout information of the processed layer and at least previous one layer and/or at least next one layer, and a computer readable medium encoded with a computer program implementing the method.

The present invention is also directed to a method for classifying defects during fabricating a semiconductor device, and a computer readable medium encoded with a computer program implementing the method.

The present invention provides a method for promoting semiconductor manufacturing yield, wherein the method comprises the following steps. First, a processed layer is inspected to generate an inspected image with defects thereon. Then, the inspected image is aligned to an original design layout information of the processed layer. In addition, the defects are classified according to geometric features of the original design layout information of the processed layer and at least previous one layer and/or at least next one layer.

The present invention further provides a computer readable medium encoded with a computer program implementing the method for promoting semiconductor manufacturing yield, wherein the method comprises the above-mentioned steps.

According to an embodiment of the present invention, the method further comprises defining at least one hotspot of the original design layout information according to at least one of the defects being classified as a defect of interest.

According to an embodiment of the present invention, the previous one layer, the processed layer and the next one layer are formed on a semiconductor substrate sequentially.

According to an embodiment of the present invention, each of the previous one layer, the processed layer and the next one layer is a metal layer, a semiconductor layer, a dielectric layer or a photo resist layer.

The present invention also provides a method for classifying defects during fabricating a semiconductor device, wherein the method comprises the following steps. First, an inspected image with the defects thereon is provided, wherein the inspected image is generated from a processed layer of a semiconductor wafer inspected by a scanning electron microscope. Then, the inspected image is aligned to an original design layout information of the processed layer. In addition, the defects are classified according to geometric features of the original design layout information of the semiconductor device.

The present invention further provides a computer readable medium encoded with a computer program implementing the method for classifying defects during fabricating a semiconductor device, wherein the method comprises the above-mentioned steps.

According to an embodiment of the present invention, the method further comprises defining at least one hotspot of the original design layout information according to at least one of the defects being classified as a defect of interest.

According to an embodiment of the present invention, the processed layer is a metal layer, a semiconductor layer, a dielectric layer or a photo resist layer.

In contrast to the conventional method for inspecting defects in a semiconductor device, the present invention can consider effect of each defect of the current layer to other layers, and effects of every defect to the current layer and/or other layers can be entirely figured out before the semiconductor device is manufactured, so as to reduce manufacturing cycle times. In addition, each defect may be classified into DOI or unimportant defect or more precisely by using the present invention, so as to define hotspot areas more accurately and further reduce manufacturing cycle times by neglecting the unimportant defects during manufacturing the semiconductor device. Accordingly, the present invention can increase or promote total yield of manufacturing the semiconductor device.

DETAILED DESCRIPTION OF THE INVENTION

Reference will now be made in detail to specific embodiments of the present invention. Examples of these embodiments are illustrated in the accompanying drawings. While the invention will be described in conjunction with these specific embodiments, it will be understood that it is not intended to limit the invention to these embodiments. In fact, it is intended to cover alternatives, modifications, and equivalents as may be included within the spirit and scope of the invention as defined by the appended claims. In the following description, numerous specific details are set forth in order to provide a through understanding of the present invention. The present invention may be practiced without some or all of these specific details. In other instances, well-known process operations are not described in detail in order not to obscure the present invention.

Figure 1:
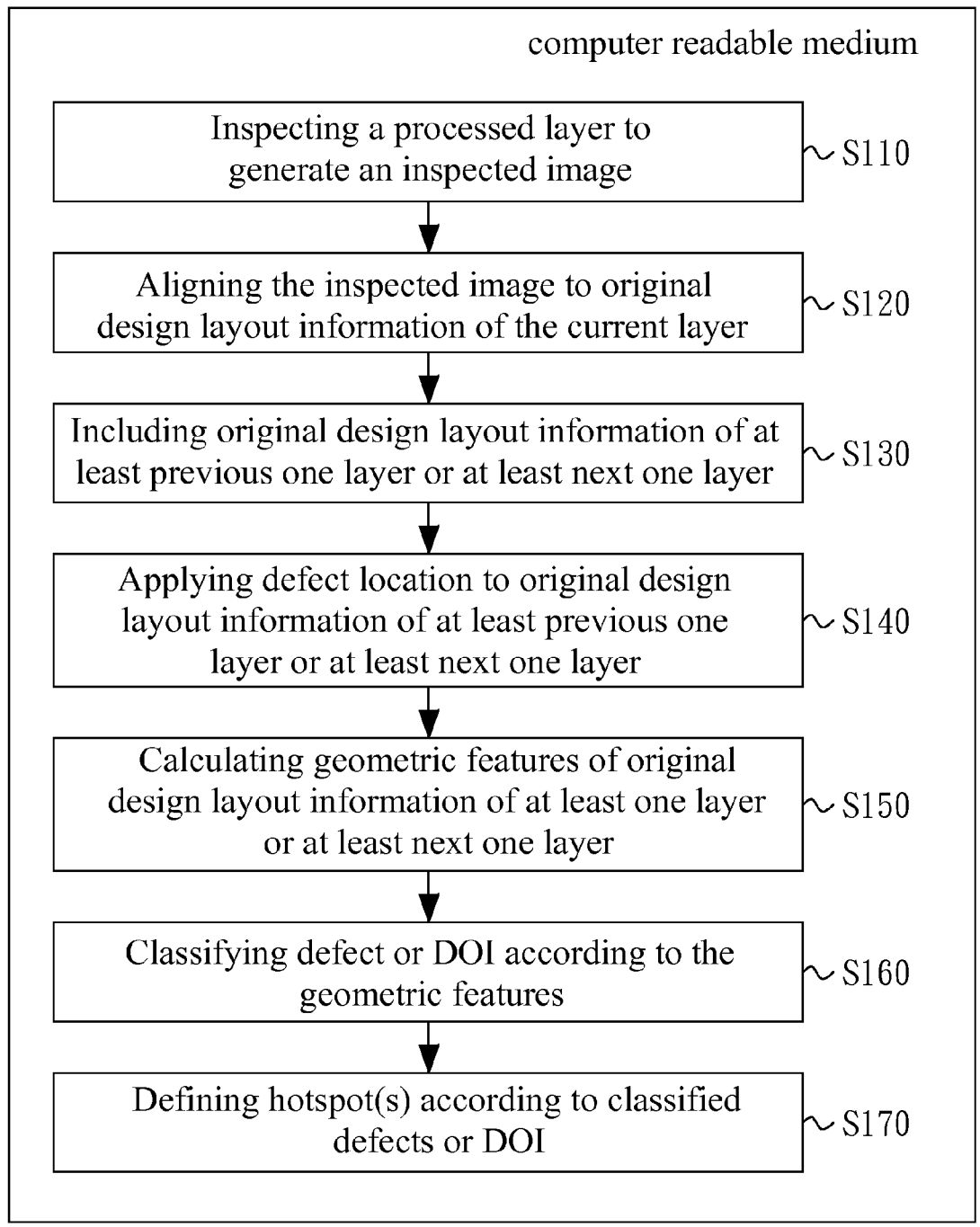
FIG. 1 illustrates a block diagram of a method for promoting semiconductor manufacturing yield according to an embodiment of the present invention.
Figure 2:
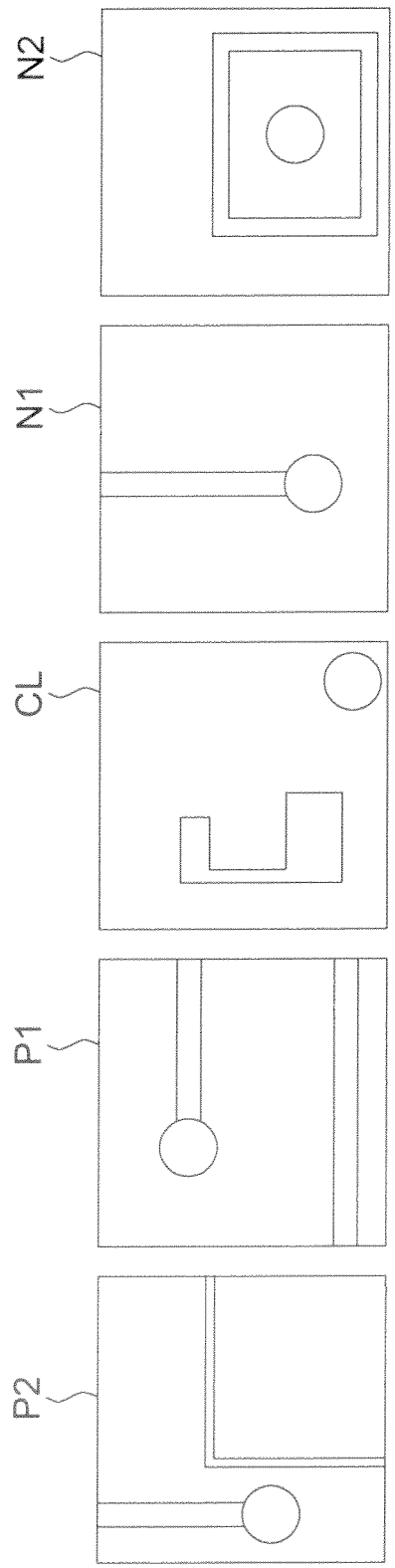
FIG. 2 illustrates original design layout information of a semiconductor device layer by layer according to an embodiment of the present invention.
Figure 3:
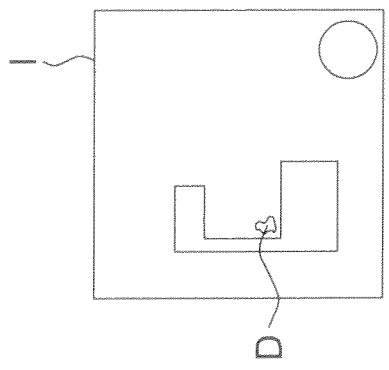
FIG. 3 illustrates an inspected image of a processed layer of a semiconductor device according to an embodiment of the present invention.
Figure 4:
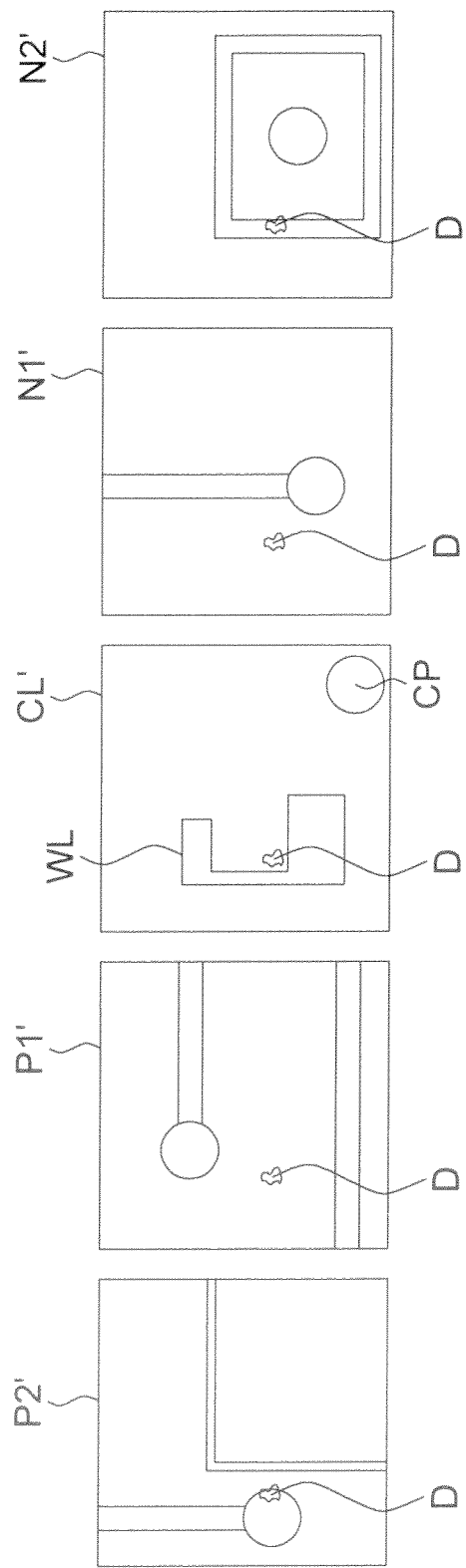
FIG. 4 illustrates the defect as shown in FIG. 3 applied to original design layout information of the previous layers, the current layer and the next layers as shown in FIG. 2.

FIG. 1 illustrates a block diagram of a method for promoting semiconductor manufacturing yield according to an embodiment of the present invention. FIG. 2 illustrates original design layout information of a semiconductor device layer by layer according to an embodiment of the present invention. FIG. 3 illustrates an inspected image of a processed layer of a semiconductor device according to an embodiment of the present invention. In addition, FIG. 4 illustrates the defect as shown in FIG. 3 applied to original design layout information of the previous layers, the current layer and the next layers as shown in FIG. 2. For simplification. FIGS. 2, 3 and 4 respectively illustrates a part of the semiconductor device only.

Referring to FIG. 2 first, original design layout information of a semiconductor device in the present embodiment may comprise, for example without limitation, two previous layers P2, P1, a current layer CL, and two next layers N1, N2. Accordingly, the semiconductor device may be manufactured on a semiconductor substrate in accordance with the original design layout information layer by layer. In the present embodiment, each of the previous layers P2, P1, the current layer CL, and the next layers N1, N2 may be original design layout information of a metal layer, a semiconductor layer, a dielectric layer or a photo resist layer of a semiconductor wafer.

Referring to FIG. 1, the method for promoting semiconductor manufacturing yield, which may be implemented by a computer program encoded within a computer readable medium, comprises the following steps. At block S110, a processed layer formed according to an original design layout information of a current layer CL as shown in FIG. 2 is inspected to generate an inspected image I with a defect D thereon as shown in FIG. 3. For example, the processed layer may be inspected by using a SEM system to generate an inspected image with gray levels, since the dielectric layer, the photo resist layer, the defect, and the conductive layer, such as the metal layer or the semiconductor layer, may have different electric conductively. In the present embodiment, the defect D may be an electric type defect, such as a voltage contrast (VC) defect, a short defect, an open defect, a parasitic capacitor defect or a cross talk defect, or a geometric type defect, such as a void defect or a critical dimension (CD) variant defect. Further, the processed layer may be also inspected by using optical system.

Then please refer to FIG. 4 for blocks S120 and S130. At block S120, the inspected image I is aligned to the current layer CL, so as to mark the location of the defect D to form the current layer CL' as shown in FIG. 4. At block S130, the previous layers P2, P1 and the next layers N1, N2 are included and the location of the defect D is applied thereon at block S140, so as to form the previous layers P2', P1' and the next layers N1', N2' as shown in FIG. 4. Therefore, at block S150, patterned geometric features of the previous layers P2, P1, the current layer CL and the next layers N1, N2 can be respectively calculated with the defect D, and then the defect D may be classified into DOI or unimportant defect at block S160 according to the patterned geometric features thereof.

For example, the defect D may not affect the current layer CL when it is a metal spot. Thus, the defect D may be classified into unimportant defect by only calculating with the current layer CL. However, the defect D may form a parasitic capacitor with wires of the previous layer P2 and the next layer N2, so as to be classified as an electric type defect into DOI by calculating with the other layers. In contract to conventional inspecting method, the present invention can consider effect of each defect of the current layer to other layers, and effects of every defect to the current layer and/or other layers can be entirely figured out before the semiconductor device is manufactured, so as to reduce manufacturing cycle times. In addition, each defect may further be classified more precisely by using the present invention.

In the present embodiment, the method may further comprise a step of defining a hotspot of at least one of the previous layers P2, P1, the current layer CL and the next layers N1, N2 at block S170, after the defect D is classified as a DOI. Herein, the hotspot is a region that a defect is easy to generate. For example, referring to FIG. 4, the defect D may not affect the previous layer P1, the current layer CL and the next layer N1, thus a hotspot according to the defect D may not be defined thereon. However, the defect D may effect to the previous layer P2 and the next layer N2, thus a hotspot according to the defect D may be defined thereon. Accordingly, hotspots and unimportant defects may be defined more accurately, so as to further reduce manufacturing cycle times by neglecting the unimportant defects during manufacturing the semiconductor device, and total yield of manufacturing the semiconductor device can be increased or promoted thereby.

Figure 5:
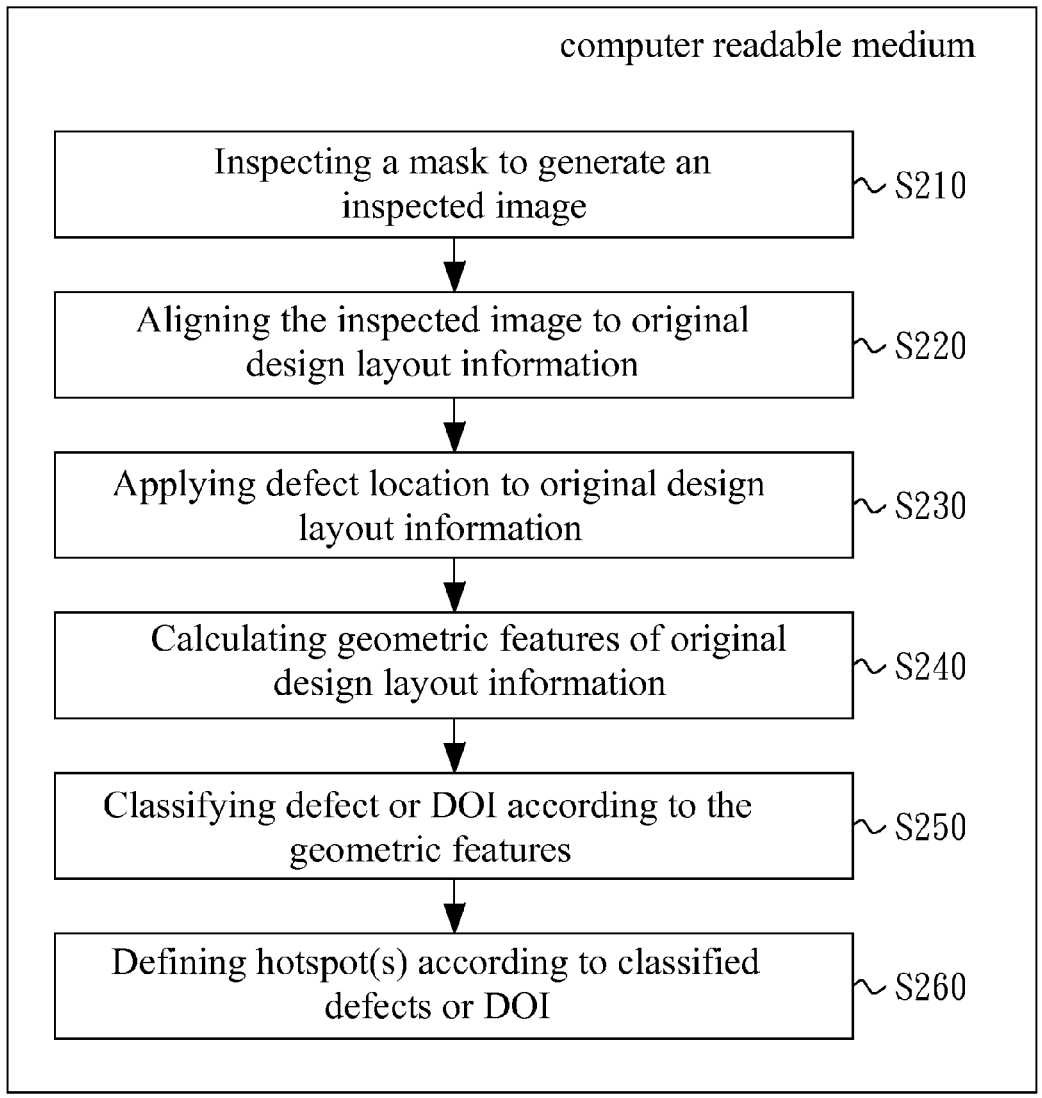
FIG. 5 illustrates a block diagram of a method for promoting semiconductor manufacturing yield according to another embodiment of the present invention.
Figure 6:
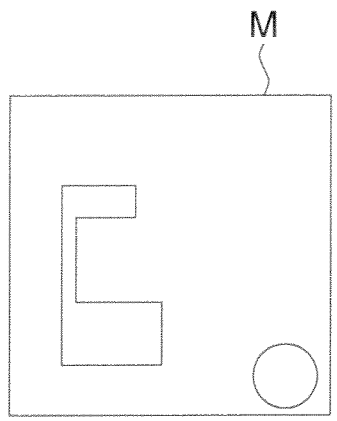
FIG. 6 illustrates original design layout information of a mask according to another embodiment of the present invention.
Figure 7:
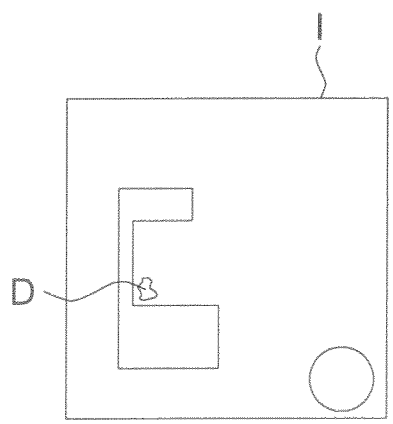
FIG. 7 illustrates an inspected image of a mask according to another embodiment of the present invention.

FIG. 5 illustrates a block diagram of a method for promoting semiconductor manufacturing yield according to another embodiment of the present invention, and FIG. 6 illustrates original design layout information of a mask according to another embodiment of the present invention. In addition, FIG. 7 illustrates an inspected image of a mask according to another embodiment of the present invention. Referring to FIG. 5, the method as shown in FIG. 5 is similar to that as shown in FIG. 1, besides the method in the present embodiment is applied to mask inspection.

In detail, the method in the present embodiment comprises the following steps. At block S210, a mask M, such as a reticle, having an original design layout information as shown in FIG. 6 is inspected to generate an inspected image I with a defect D thereon as shown in FIG. 7. At block S220, the inspected image I is aligned to the original design layout information to mark the location of the defect D. At block S230, the location of the defect D is applied to the original design layout information, so as to calculate geometric features with the defect D at block S240. Accordingly, the defect D may be classified into DOI or unimportant defect at block S250 according to the geometric features thereof, and then a hotspot of the mask M may be defined at block S260, after the defect D is classified as a DOI.

In summary, the present invention inspects defects and takes consideration entirely about effects of defects of current layer to other layer, so as to reduce manufacturing cycle times. In addition, each defect may be classified into DOI or unimportant defect or more precisely to define hotspot areas more accurately, so as to further reduce manufacturing cycle times by neglecting the unimportant defects during manufacturing the semiconductor device. Accordingly, the present invention can increase or promote total yield of manufacturing the semiconductor device.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims.

What is claimed is:

1. A method for promoting semiconductor manufacturing yield of a multilayered device, comprising steps of:
    inspecting a processed layer of the multilayered device to identify defects such that an inspected image with the defects thereon is generated;
    aligning the inspected image to an original design layout information of the processed layer to determine the locations of the defects in the processed layer; and
    classifying the defects on the inspected image according to the locations of the defects, patterned geometric features of the original design layout information of the processed layer and patterned geometric features of at least one previous layer and/or at least one next layer of the multilayered device.

2. The method as claimed in claim 1, further comprising defining at least one hotspot of the original design layout information according to at least one of the defects being classified as a defect of interest.

3. The method as claimed in claim 1, wherein the at least one previous layer, the processed layer, and the at least one next layer are formed on a semiconductor substrate sequentially.

4. The method as claimed in claim 1, wherein each of the at least one previous layer, the processed layer, and the at least one next layer is a metal layer, a semiconductor layer, a dielectric layer, or a photo resist layer.

5. A method for classifying defects during fabricating a semiconductor device, comprising steps of:
    providing an inspected image with defects thereon, wherein the inspected image is generated from inspecting a processed layer of a semiconductor wafer inspected by a scanning electron microscope to identify the defects;
    aligning the inspected image to an original design layout information of the processed layer to determine the locations of the defects in the processed layer; and
    classifying the defects on the inspected image according to the locations of the defects, patterned geometric features of the original design layout information of the processed layer and patterned geometric features of at least one previous layer and/or at least one next layer of the semiconductor device.

6. The method as claimed in claim 5, further comprising defining at least one hotspot of the original design layout information according to at least one of the defects being classified as a defect of interest.

7. The method as claimed in claim 5, wherein the processed layer is a metal layer, a semiconductor layer, a dielectric layer or a photo resist layer.

8. A non-transitory computer readable medium encoded with a computer program implementing a method for promoting semiconductor manufacturing yield of a multilayered device and the method comprises steps of:
    inspecting a processed layer of the multilayered device to identify defects such that an inspected image with the defects thereon is generated;
    aligning the inspected image to an original design layout information of the processed layer to determine the locations of the defects in the processed layer; and
    classifying the defects on the inspected image according to the locations of the defects, patterned geometric features of the original design layout information of the processed layer and patterned geometric features of at least one previous layer and/or at least one next layer of the multilayered device respectively.

9. The non-transitory computer readable medium as claimed in claim 8, wherein the method further comprises defining at least one hotspot of the original design layout information according to at least one of the defects being classified as a defect of interest.

10. The non-transitory computer readable medium as claimed in claim 8, wherein the at least one previous layer, the processed layer, and the at least one next layer are formed on a semiconductor substrate sequentially.

11. The non-transitory computer readable medium as claimed in claim 8, wherein each of the at least one previous layer, the processed layer, and the at least one next layer is a metal layer, a semiconductor layer, a dielectric layer, or a photo resist layer.

12. A non-transitory computer readable medium encoded with a computer program implementing a method for classifying defects during fabricating a semiconductor device and the method comprises steps of:
    providing an inspected image with defects thereon, wherein the inspected image is generated from inspecting a processed layer of a semiconductor wafer inspected by a scanning electron microscope to identify the defects;
    aligning the inspected image to an original design layout information of the processed layer to determine the locations of the defects in the processed layer; and
    classifying the defects on the inspected image according to the locations of the defects, patterned geometric features of the original design layout information of the processed layer and patterned geometric features of at least one previous layer and/or at least one next layer of the semiconductor device.

13. The non-transitory computer readable medium as claimed in claim 12, wherein the method further comprises defining at least one hotspot of the original design layout information according to at least one of the defects being classified as a defect of interest.

14. The non-transitory computer readable medium as claimed in claim 12, wherein the processed layer is a metal layer, a semiconductor layer, a dielectric layer or a photo resist layer.

\* \* \* \* \*